US009927371B2

(12) United States Patent
Wang et al.

(10) Patent No.: US 9,927,371 B2
(45) Date of Patent: Mar. 27, 2018

(54) CONFOCAL LINE INSPECTION OPTICAL SYSTEM

(71) Applicant: KLA-Tencor Corporation, Milpitas, CA (US)

(72) Inventors: Mark S. Wang, San Ramon, CA (US); Chris Kirk, Buckinghamshire (GB); Andrey Kharisov, Saratoga, CA (US)

(73) Assignee: KLA-Tencor Corporation, Milpitas, CA (US)

( * ) Notice: Subject to any disclaimer, the term of this patent is extended or adjusted under 35 U.S.C. 154(b) by 55 days.

(21) Appl. No.: 14/691,966

(22) Filed: Apr. 21, 2015

(65) Prior Publication Data

US 2015/0369750 A1 Dec. 24, 2015

Related U.S. Application Data

(60) Provisional application No. 61/982,754, filed on Apr. 22, 2014.

(51) Int. Cl.
| | |
|---|---|
| *G01N 21/00* | (2006.01) |
| *G01N 21/88* | (2006.01) |
| *G02B 21/00* | (2006.01) |
| *G02B 21/36* | (2006.01) |
| *G01N 21/95* | (2006.01) |
| *H01L 21/66* | (2006.01) |

(52) U.S. Cl.
CPC ..... *G01N 21/8851* (2013.01); *G01N 21/9501* (2013.01); *G02B 21/0028* (2013.01); *G02B 21/0032* (2013.01); *G02B 21/0072* (2013.01); *G02B 21/365* (2013.01); *G01N 2201/068* (2013.01); *G01N 2201/10* (2013.01); *G01N 2201/121* (2013.01); *H01L 22/12* (2013.01)

(58) Field of Classification Search
CPC ........... G01N 21/8851; G01N 21/9501; G01N 2201/068; G01N 2201/10; G01N 2201/121; G01N 21/8806; G01N 21/95623; G01N 21/956; G01N 21/9503; G01N 2021/8867; G02B 21/0032; G02B 21/0072; G02B 21/365; H01L 22/12
USPC ...................................................... 356/237.5
See application file for complete search history.

(56) References Cited

U.S. PATENT DOCUMENTS

| | | | |
|---|---|---|---|
| 5,965,910 | A | 10/1999 | Wood |
| 6,128,077 | A | 10/2000 | Jovin et al. |
| 6,384,910 | B2 | 5/2002 | Vaez-Iravani et al. |
| 7,525,649 | B1 | 4/2009 | Leong et al. |

(Continued)

OTHER PUBLICATIONS

PCT International Search Report for International Application No. PCT/US2015/027162, dated Aug. 26, 2015, 4 pages.

*Primary Examiner* — Sunghee Y Gray
(74) *Attorney, Agent, or Firm* — Suiter Swantz pc llo

(57) ABSTRACT

A line scan wafer inspection system includes a confocal slit aperture filter to remove sidelobes and enhance resolution in the scanning direction. A position detector associated with the slit aperture filter monitors and corrects illumination line image positions relative to the slit aperture to keep image position variations within tolerable limits. Each detector measures a line position and then uses the line position signal to adjust optical, mechanical, and electronic components in the collection path in a feedback loop. The feedback loop may be employed in a runtime calibration process or during inspection to enhance stability.

14 Claims, 7 Drawing Sheets

(56) References Cited

U.S. PATENT DOCUMENTS

| | | |
|---|---|---|
| 2002/0163717 A1 | 11/2002 | Lee |
| 2005/0018180 A1 | 1/2005 | Ayres |
| 2008/0281556 A1* | 11/2008 | Matsuzawa ........ G01M 11/0257 |
| | | 702/155 |
| 2010/0188742 A1* | 7/2010 | Chen .................. G02B 21/0032 |
| | | 359/385 |
| 2012/0113506 A1* | 5/2012 | Gmitro .............. G02B 21/0028 |
| | | 359/385 |
| 2013/0155500 A1 | 6/2013 | Yoshida et al. |
| 2013/0215404 A1* | 8/2013 | Den Boef ............. G01J 3/4412 |
| | | 355/44 |

\* cited by examiner

CONFOCAL LINE INSPECTION OPTICAL SYSTEM

PRIORITY

The present application claims the benefit under 35 U.S.C. § 119(e) of U.S. Provisional Application Ser. No. 61/982,754, filed Apr. 22, 2014, which is incorporated herein by reference.

FIELD OF THE INVENTION

The present disclosure is directed generally toward wafer inspection systems, and more particularly toward line scan inspection devices with confocal scanning elements.

BACKGROUND

In confocal microscopy, a pinhole filter in the confocal plane of the lens eliminates unfocussed light. However, because confocal pinhole filters clip illumination lines projected to the sensor; any shift of that line relative to the pinhole filter will result in a change of the image intensity.

While improving resolution, confocal pinhole filters also increase tool sensitivity to focus and boresight variation due to thermal drifts, vibrations and mechanical repeatability of components. Increased sensitivity affects stability of the tool and eliminating all of the increased sensitivity factors is impractical due to tool complexity.

Consequently, it would be advantageous if an apparatus existed that is suitable for wafer inspection with confocal slit aperture filters and increase stability.

SUMMARY

Accordingly, the present invention is directed to a novel apparatus for wafer inspection with confocal slit aperture filters and increase stability.

In one embodiment, a line scan wafer inspection system includes a detector associated with each slit aperture filter in the confocal plane to monitor and correct line positions relative to the slit aperture filter to keep image intensity variations within tolerable limits. Each detector measures a line position and then uses the line position signal to adjust optical components in the collection path in a feedback loop.

In one embodiment, the feedback loop is employed in a runtime calibration process. In another embodiment, the feedback loop is employed as a real-time compensation mechanism during inspection to enhance stability.

It is to be understood that both the foregoing general description and the following detailed description are exemplary and explanatory only and are not restrictive of the invention claimed. The accompanying drawings, which are incorporated in and constitute a part of the specification, illustrate an embodiment of the invention and together with the general description, serve to explain the principles.

BRIEF DESCRIPTION OF THE DRAWINGS

The numerous advantages of the present disclosure may be better understood by those skilled in the art by reference to the accompanying figures in which.

DETAILED DESCRIPTION

Reference will now be made in detail to the subject matter disclosed, which is illustrated in the accompanying drawings. The scope of the invention is limited only by the claims; numerous alternatives, modifications and equivalents are encompassed. For the purpose of clarity, technical material that is known in the technical fields related to the embodiments has not been described in detail to avoid unnecessarily obscuring the description.

An understanding of one or more embodiments of the present disclosure may be further illuminated by U.S. Pat. No. 7,525,649 which is hereby incorporated by reference.

Figure 1A:
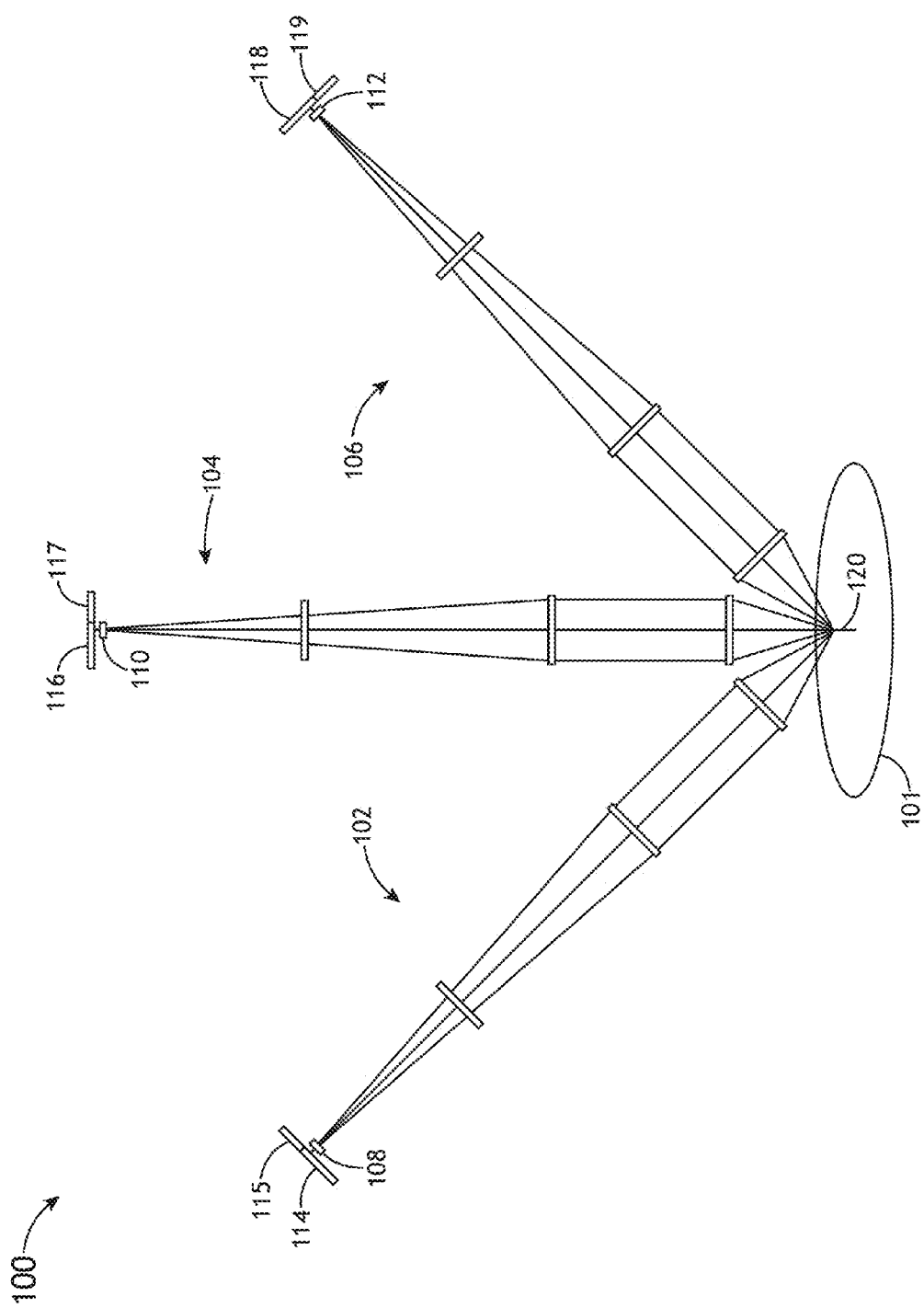
FIG. 1A shows a front view of a wafer inspection system according to one embodiment of the present disclosure.

Referring to FIG. 1A, a front view of a wafer inspection system according to one embodiment of the present disclosure is shown. In some embodiments, a wafer inspection system, such as a line scan optical inspection system 100 includes three collection channels 102, 104, 106 to collect scattered light from defects in a wafer 101 and image the light onto corresponding array line sensors 114, 116, 118. A position detector 115, 117, 119 is associated with each array line sensor 114, 116, 118. In some embodiments, illumination optics form a thin line 120 at a scanning location on the wafer 101. Scattered light from the illuminated scanning location on the wafer 101 is gathered and focused by the three collection channels 102, 104, 106 onto each array line sensor 114, 116, 118. In one exemplary embodiment, the thin line 120 may have, but is not required to have, a width less than 1 micrometer on the wafer 101. Scattered light from wafer 101 features and defects are imaged onto the array line sensors 114, 116, 118 in each collection channel 102, 104, 106. The array line sensors 114, 116, 118 may include any imaging technology known in the art. In some embodiments, array line sensors 114, 116, 118 include charge coupled devices (CCD) or time-delayed integration (TDI) devices.

In some embodiments, each array line sensor 114, 116, 118 is associated with a slit aperture filter 108, 110, 112. In at least one embodiment, where the line scan optical inspection system 100 includes a line illumination device, the array line sensors 114, 116, 118 may be configured for a large field of view in the x-direction (perpendicular to the illuminated line 120) to collect all scattered light. The position detectors 115, 117, 119 are positioned just outside of the corresponding array line sensor 114, 116, 118 in y-direction (along the long axis of the illuminated line 120). These position detectors 115, 117, 119 tracks light scattered from wafer 101 and compare the position of the scattered light against a calibrated position corresponding to the center of a corresponding slit aperture filter 108, 110, 112. An error signal generated by the position detectors 115, 117, 119 is used to move an optical element in the corresponding collection channel 102, 104, 106 to ensure scattered light from wafer 101 is centered on the slit aperture filter 108, 110, 112. A person skilled in the art may appreciate that while the position detectors 115, 117, 119 in FIG. 1 are shown offset the array line sensors 114, 116, 118 in a direction perpendicular to the illumination line 120, such illustration is merely a function of the limitations of a two-dimensional medium.

In some embodiments, slit aperture filters 108, 110, 112 substantially abut the corresponding array line sensors 114, 116, 118. In other embodiments, where the slit aperture filters 108, 110, 112 are separated from the corresponding array line sensors 114, 116, 118 by some distance, a cylinder lens may re-focus light to the slit aperture filters 108, 110, 112.

For line scan inspection tools, the resolution in the wafer 101 scanning direction may be determined by an illumination line profile. Resolution in the x-direction may be determined by the illumination line width. The line width may be limited by the numerical aperture (NA) of the line formation cylinder (LFC) which has a theoretical limit of 1, and by the Gaussian beam at the entrance pupil. It is noted that a smaller line width may be achieved with a more aggressive Gaussian fill factor, but sidelobes from diffraction ringing create a performance limitation. A confocal slit aperture filter at the detector enhances the resolution in the scanning direction beyond this limitation. In a line scan optical inspection system 100, a confocal slit aperture filter 108, 110, 112 at each array line sensor 114, 116, 118 enhances the resolution in the scanning direction and suppresses sensitivity to illumination line sidelobes.

When a point scans across the wafer 101 in the direction perpendicular to the illumination line (x-direction), the image produced on an array line sensor 114, 116, 118 can be described using a point spread function defined for each collection channel 102, 104, 106:

$$F_{PS\_Channel}(X,Y,Z)$$

where X, Y are local coordinates for each array line sensor 114, 116, 118 and Z is a defocus value when the illuminated point is not at the array line sensor 114, 116, 118 conjugate. The illumination line spread function is described by:

$$F_{PS\_Illumination}(xw)$$

at the wafer coordinate xw.

Given a magnification M for a collection channel 102, 104, 106, the overall point spread function, including the illumination profile is:

$$F_{PS}(xw,yw,X) = F_{PS\_Illumination}(xw) * F_{PS\_Channel}(X-M*xw, M*yw, Z)$$

Integrated over the length of the array line sensor 114, 116, 118 over X.

For a center collection channel 104, Z is constant, with a narrow slit aperture filter 110, centered at X=0:

$$F_{PS}(xw,yw) = F_{PS\_Illumination}(xw) * F_{PS\_Center}(-M*xw, M*yw, Z)$$

In one embodiment, if both point spread functions have a Gaussian shape, $\exp(-X^2/W^2)$, the system point spread function is also Gaussian, with a width W ($W_{IL}$ of the illumination point spread function and $W_C$ channel point spread function), calculated as:

$$1/W^2 = 1/W_{IL}^2 + 1/W_C^2$$

Such a point spread function may have a smaller line width and higher resolution. With large slit aperture filter 108, 110, 112 width, after integration of the channel point spread function, the line width in the x-direction is determined by the illumination line width only. It is noted that at least in some instances a narrow slit aperture filter 108, 110, 112 will not collect sidelobe energy, but a wide slit aperture filter 108, 110, 112 will collect sidelobe energy.

It is further noted that a similar effect is observed in the case of a side collection channel 114, 118. In this case, for large slit aperture filter 108, 110, 112 and detector 114, 116, 118 width, the overall line width is determined by the illumination line width. Further, for a slit aperture filter 108, 110, 112, line width is reduced because of a multiplication factor.

When a narrow slit aperture filter 108, 110, 112 is implemented, either mechanically or electronically at the sensor, sidelobes can be suppressed significantly. Suppressing sidelobes allows for higher resolution with smaller line width. Properly suppressing sidelobes requires the focused light to be correctly centered on the slit in the slit aperture filter 108, 110, 112; therefore position detectors 115, 117, 119 that allow the line illumination system 100 to alter the position of optical elements in one or more of the collection channels 102, 104, 106 is desirable. However, inspection sensitivity may suffer because a slit aperture filter 108, 110, 112 will necessarily cause a degree of light loss. It is, therefore, important that the slit aperture filter 108, 110, 112 be replaceable when more light is needed. A system including mechanical slit aperture filters 108, 110, 112 may include a mechanism for swapping such slit aperture filters. Alternatively, a system including electronic slit aperture filters 108, 110, 112 may be configured such that the electronic slit aperture filters may be adjusted with different slit aperture widths for different applications.

Figure 1B:
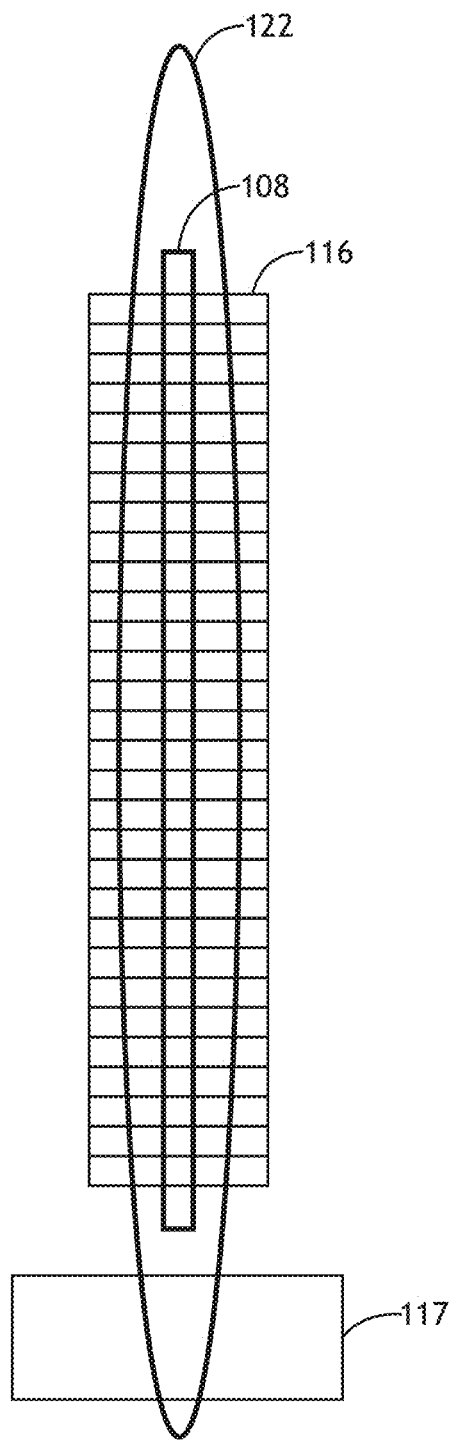
FIG. 1B shows a detailed top view of one image sensor and position detector pair.

Referring to FIG. 1B, a detailed top view of one image sensor and position detector pair is shown. In one exemplary embodiment, the first collection channel of FIG. 1A has an associated image sensor 116 and position detector 117. An illumination line image 122 from the first collection channel illuminates both the image sensor 116 and position detector 117. The portion of the illumination line image 122 that illuminates the image sensor would be filtered by a corresponding slit aperture filter 108 while the portion illuminating the position detector 117 would not. The position detector 117 produces a signal corresponding to the position of the illumination line image 122 in the scanning direction (x-direction). In some embodiments, similar image sensor 116/position detector 117 pairs are used for each collection channel.

Figure 2:
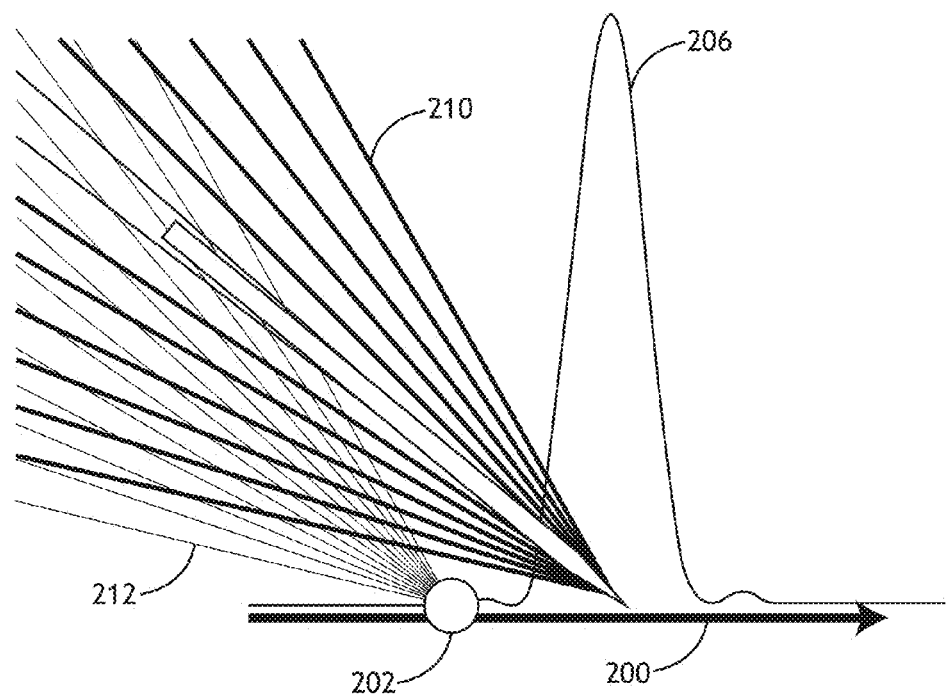
FIG. 2 shows a close-up representation of wafer light scattered in a moving wafer inspection system.

Referring to FIG. 2, a close-up representation of wafer light scattered in a moving wafer inspection system is shown. In a wafer inspection process, a wafer is illuminated by a line illumination source having an illumination profile 206 as the wafer moves in a direction of travel 200. Primary light 210 is scattered by the wafer to be received and focused by one or more collection channels. Furthermore, secondary light 212 may be scattered by undesirable structures 202.

Figure 3:
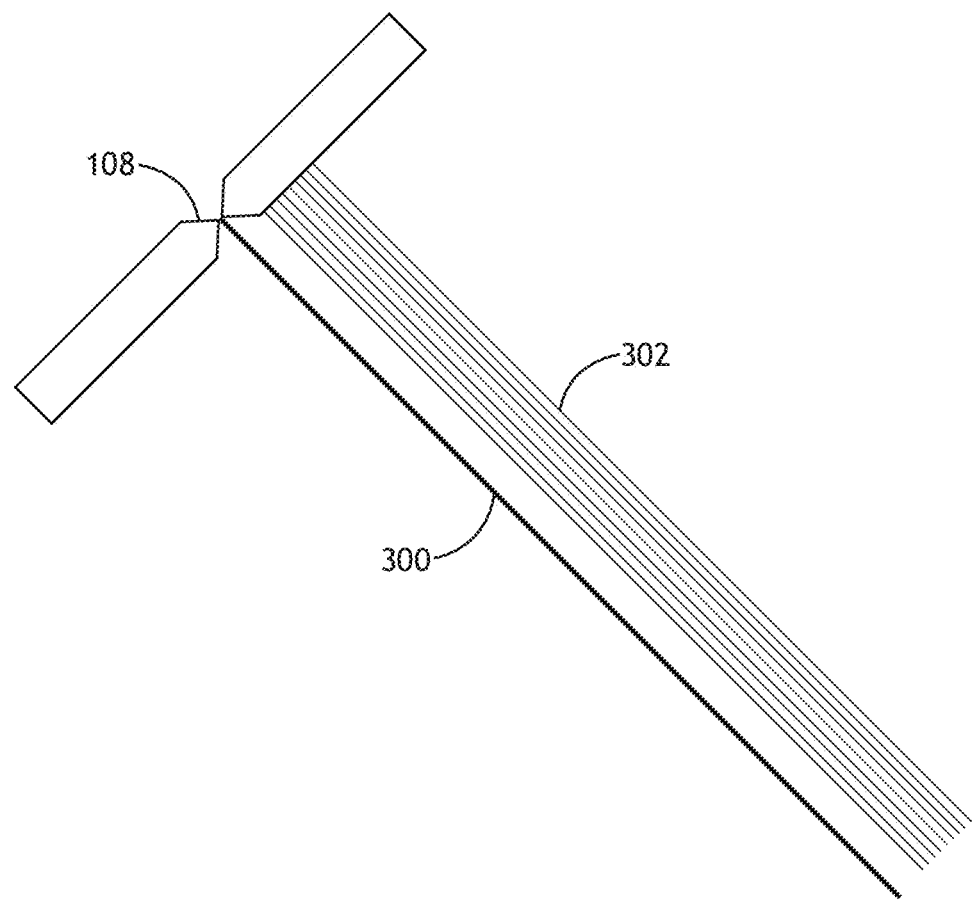
FIG. 3 shows a close-up of a portion of the wafer inspection system of FIG. 1.

Referring to FIG. 3, a close-up of a portion of the wafer inspection system of FIG. 1 is shown. In at least one embodiment of the present disclosure, a first slit aperture filter 108 is associated with a first collection channel. The first slit aperture filter 108 is positioned and oriented in the confocal plane as defined by the first collection channel optics. The first slit aperture filter 108 transmits a primary beam 300 associated with the primary light scattered by the wafer by the line illumination source, and filters out incidental beams 302 associated with the secondary light or sidelobes of the line illumination beam scattered by the wafer.

In at least one embodiment, the first slit aperture filter 110 comprises a mechanical filter. The mechanical filter may be replaceable with mechanical filters having larger slit apertures to allow more light where increased sensitivity is required. Alternatively, in at least one embodiment, the first slit aperture filter 108 comprises an electronic filter. The electronic filter may be adjustable to produce a larger or smaller aperture as desired for system sensitivity for particular applications.

Figure 4:
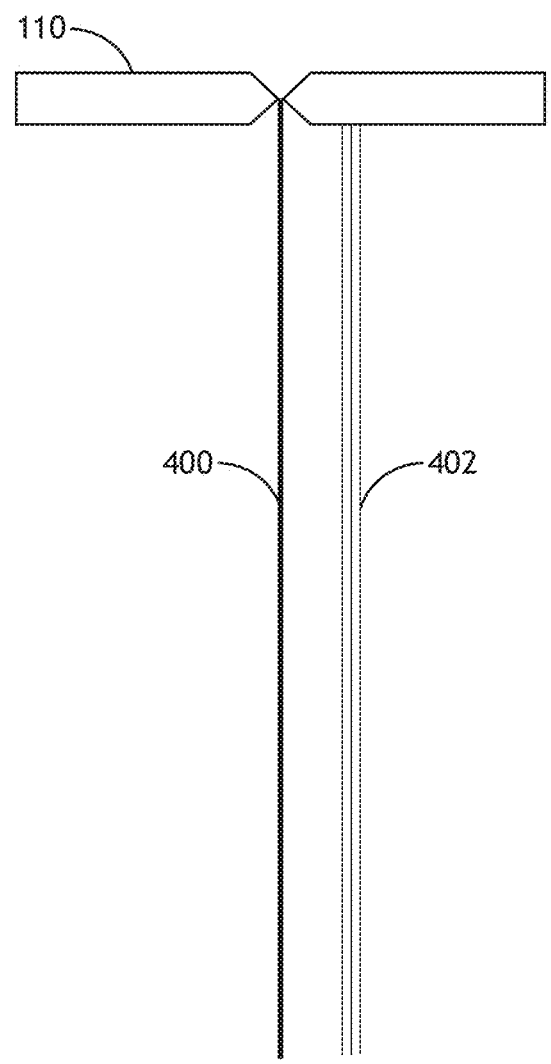
FIG. 4 shows a close-up of a portion of the wafer inspection system of FIG. 1.

Referring to FIG. 4, a close-up of a portion of the wafer inspection system of FIG. 1 is shown. In at least one embodiment of the present disclosure, a second slit aperture filter 110 is associated with a second collection channel. The second slit aperture filter 110 is positioned and oriented in the confocal plane as defined by the second collection channel optics. The second slit aperture filter 110 transmits a primary beam 400 associated with the primary light scattered by the wafer by the line illumination source, and filters out incidental beams 402 associated with the secondary light or sidelobes of the line illumination beam scattered by the wafer.

In at least one embodiment, the second slit aperture filter 110 comprises a mechanical filter. The mechanical filter may be replaceable with mechanical filters having larger slit apertures to allow more light where increased sensitivity is required. Alternatively, in at least one embodiment, the second slit aperture filter 110 comprises an electronic filter. The electronic filter may be adjustable to produce a larger or smaller aperture as desired for system sensitivity.

Figure 5:
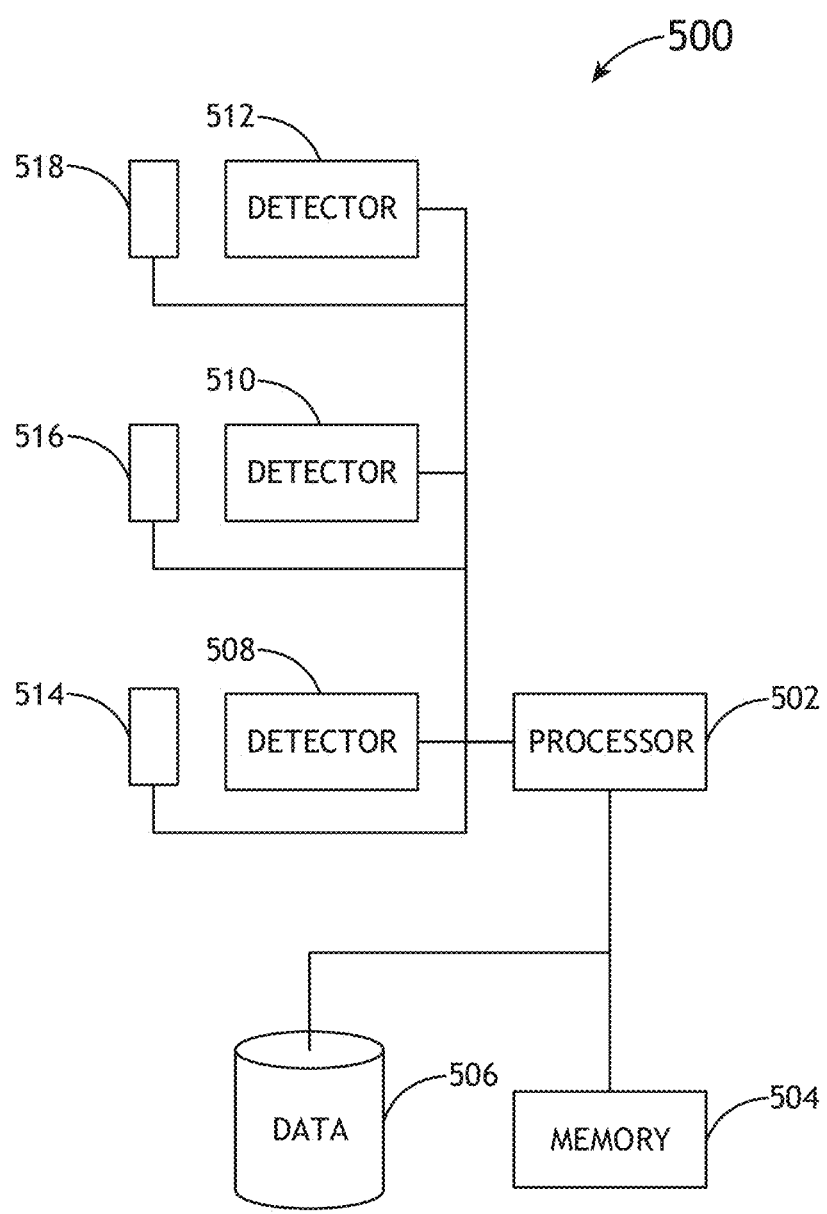
FIG. 5 shows a block diagram of a computer system for implementing embodiments of the present disclosure.

Referring to FIG. 5, a block diagram of a computer system 500 for implementing embodiments of the present disclosure is shown. The computer system 500 includes a processor 502, memory 504 connected to the processor 502 for embodying processor executable program code, and one or more detectors 508, 510, 512 connected to the processor 502. In some embodiment, each of the one or more detectors 508, 510, 512 are associated with a collection channel. In some embodiments, the computer system 500 includes a data storage element 506 connected to the processor 502. In some embodiments, the data storage element 506 is configured to store one or more illumination profiles and one or more line images received from the one or more detectors 508, 510, 512.

In some embodiments, the computer system 500 may further include an electronic aperture 514, 516, 518 associated with each detector 508, 510, 512 and connected to the processor 502. In some embodiments, the electronic apertures 514, 516, 518 may be adjustable to produce larger or smaller slit apertures as necessary.

Figure 6:
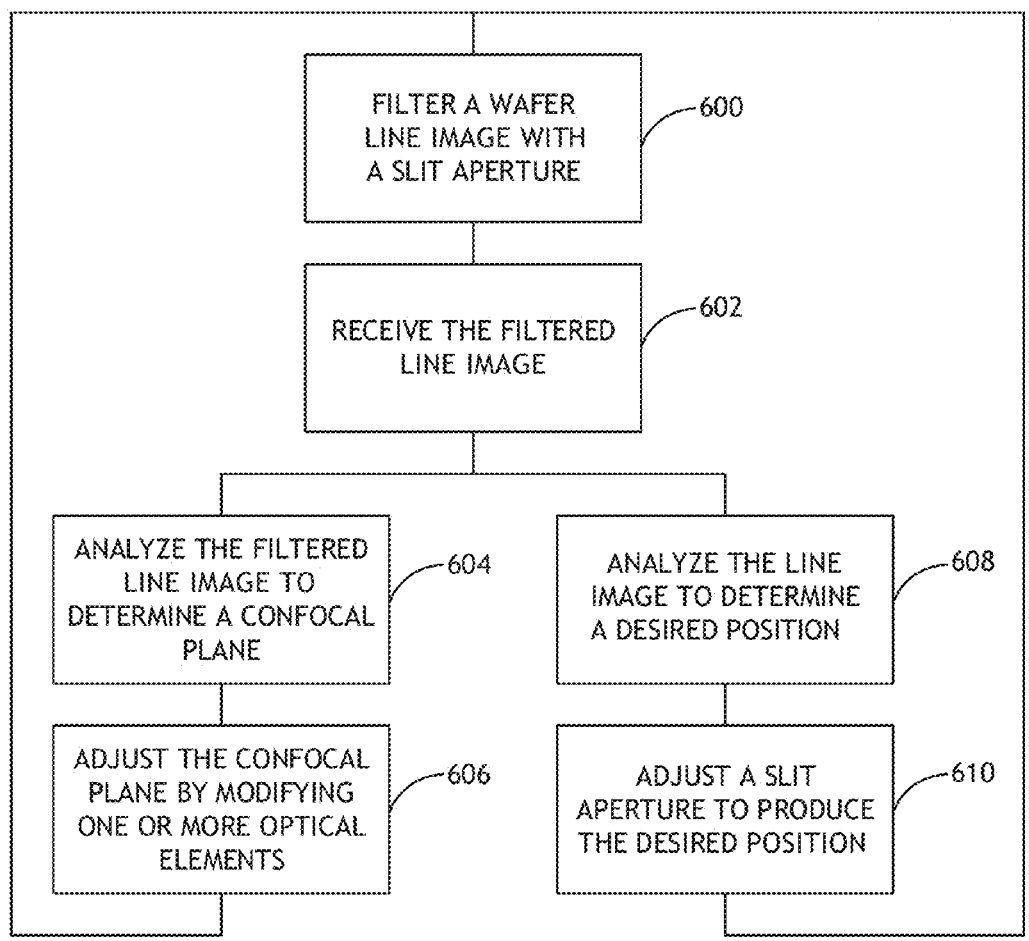
FIG. 6 shows a flowchart for a method of adjusting inspection optics in a line illumination wafer inspection system.

Referring to FIG. 6, a flowchart depicting a method of adjusting inspection optics in a line illumination wafer inspection system is shown, in accordance with an embodiment of the present disclosure. In a first step 600, in an inspection system, a wafer illumination line image from one or more collection channels is filtered with a corresponding slit aperture. In a second step 602, one or more detectors receive the illumination line image.

In a third step 604, a processor connected to the one or more detectors analyzes the illumination line image to determine if the collection channel is configured to focus the illumination line image at a predetermined confocal plane position. In a fourth step 606, the processor adjusts the confocal plane of the collection channel. The confocal plane may be adjusted by altering the relative or absolute positions of one or more optical elements in the collection channel, altering a mechanical element in the line illumination wafer inspection system performing the wafer inspection processes, altering an electronic or optical element in the illumination device creating the thin line illumination, or altering an electrical component in the line illumination wafer inspection system performing the wafer inspection process.

Alternatively, a processor connected to the one or more detectors will analyze 608 the illumination line image to determine if the illumination line image at the detector is at a desired position. The processor may then adjust 610 the position of the slit aperture, the position of one or more optical elements in a corresponding collection channel, a mechanical element in the line illumination wafer inspection system performing the wafer inspection processes, an electronic or optical element in the illumination device creating the thin line illumination, or an electrical component in the line illumination wafer inspection system performing the wafer inspection process to move the illumination line image to the desired position.

In any embodiment, the inspection system may filter 600 and receive 602 subsequent illumination line images in a feedback loop adjustment process.

It is believed that the present invention and many of its attendant advantages will be understood by the foregoing description of embodiments of the present invention, and it will be apparent that various changes may be made in the form, construction, and arrangement of the components thereof without departing from the scope and spirit of the invention or without sacrificing all of its material advantages. The form herein before described being merely an explanatory embodiment thereof, it is the intention of the following claims to encompass and include such changes.

What is claimed is:

1. A wafer inspection system comprising:
   one or more collection channels, at least one of the one or more collection channels comprising:
      a plurality of optical elements configured to collect light from a wafer being inspected and provide a line image of the wafer to a confocal plane of the at least one of the one or more collection channels in response to illumination from a line illumination system;
      a position detector configured to receive at least a portion of the line image of the wafer;
      a slit aperture filter located at the confocal plane, wherein the slit aperture filter is configured to filter out sidelobes from the line image of the wafer;
      an image sensor configured to receive the line image filtered by the slit aperture filter; and
      a processor connected to the position detector, the processor configured to:
      receive a line position signal from the position detector indicative of a position of the at least a portion of the line image of the wafer on the position detector; and
      alter the position of the line image of the wafer on the image sensor based on the line position signal.

2. The wafer inspection system of claim 1, wherein the processor connected to the position detector is further configured to:
   analyze the line position signal to determine a position of the line image of the wafer on the image sensor; and
   adjust at least one of a position of one or more optical elements in the one or more collection channels, a position of one or more mechanical elements in the wafer inspection system, an electrical component in the wafer inspection system, or an optical or electronic element of an illumination device in the wafer inspection system to alter the position of the line image of the wafer on the image sensor based on the line position signal.

3. The wafer inspection system of claim 1, further comprising:

a processor connected to the one or more position detectors, the processor configured to:
  receive one or more illumination line image signals from the one or more position detectors;
  analyze the one or more illumination line image signals to determine a confocal plane beam position associated with the collection channel in the one or more collection channels associated with one of the one or more position detectors and a corresponding one of the one or more slit aperture filters; and
  adjust at least one of a position of one or more optical elements in the collection channel, a mechanical element in the wafer inspection system, or an electrical component in the wafer inspection system to produce a desired confocal plane beam position corresponding to the one of the one or more slit aperture filters.

4. The wafer inspection system of claim 3, wherein the processor is further configured to:
  receive one or more illumination line image signals from the one or more position detectors;
  analyze the one or more illumination line image signals to determine a position of a filtered illumination line image projected on the associated image sensor; and
  adjust at least one of a position of one or more optical elements in the one or more collection channels, a mechanical element in the wafer inspection system, or an electrical component in the wafer inspection system to alter the position of an illumination line image relative to the associated image sensor.

5. The wafer inspection system of claim 4, further comprising:
  a processor connected to the one or more position detectors, the processor configured to:
    receive one or more illumination line image signals from the one or more position detectors;
    analyze the one or more illumination line image signals to determine a position of the illumination line image; and
    adjust a position of a corresponding slit aperture filter such that a slit of the slit aperture filter is centered on the illumination line image in an x-direction.

6. The wafer inspection system of claim 1, further comprising:
  a processor connected to the one or more position detectors, the processor configured to:
    receive one or more illumination line image signals from the one or more position detectors;
    analyze the one or more illumination line image signals to determine a position of a filtered illumination line image projected on the associated image sensor; and
    adjust a position of a corresponding slit aperture filter such that a slit of the slit aperture filter is centered on an illumination line image in an x-direction.

7. An apparatus comprising:
  a processor;
  memory connected to the processor configured to embody processor executable code;
  one or more image sensors connected to the processor and configured to receive one or more line images in a wafer inspection process;
  one or more position detectors connected to the processor configured to provide positions of the one or more line images on the one or more image sensors; and
  one or more slit aperture filters located at one or more confocal planes of one or more collection channels including the one or more image sensors, wherein at least one of the one or more slit aperture filters is configured to filter out sidelobes from a line image received by an image sensor of the one or more image sensors, wherein the processor executable code configures the processor to:
    receive the one or more line images from the one or more image sensors;
    analyze the one or more illumination line images; and
    alter a position of at least one of the one or more line images on at least one of the one or more image sensors.

8. The apparatus of claim 7,
  wherein the processor executable code further configures the processor to:
  adjust at least one of a position of one or more optical elements in one or more collection channels, a position of one or more mechanical elements in an apparatus performing the wafer inspection processes, or an electrical component in the apparatus performing the wafer inspection process to alter a position of at least one of the one or more line images on at least one of the one or more image sensors.

9. The apparatus of claim 8, further comprising a data storage element connected to the processor, wherein the processor executable code further configures the processor to:
  compare the positions of the one or more line images on the one or more image sensors to one or more calibrated positions associated with center positions of the one or more slit aperture filters stored in the data storage element; and
  adjust the position of at least one of the one or more line images on the at least one of the one or more image sensors to a corresponding calibrated position of the one or more calibrated positions.

10. The apparatus of claim 7, wherein analyzing the one or more line images includes determining locations of the one or more confocal planes, wherein the processor executable code further configures the processor to:
  adjust at least one of a position of one or more optical elements in the collection channel, a position of one or more mechanical elements in an apparatus performing the wafer inspection processes, or an electrical component in the apparatus performing the wafer inspection process to alter the location of at least one of the one or more confocal planes.

11. The apparatus of claim 10, further comprising:
  one or more position detectors connected to the processor configured to provide positions of the one or more line images on the one or more image sensors, wherein the processor executable code further configures the processor to:
    adjust at least one of a position of one or more optical elements in the collection channel, a position of one or more mechanical elements in an apparatus performing the wafer inspection processes, an electrical component in the apparatus performing the wafer inspection process, or an optical or electronic element of an illumination device associated with the apparatus performing the wafer inspection process to adjust a position of at least one of the one or more illumination line images on at least one of the one or more image sensors.

12. The apparatus of claim 10, further comprising a data storage element connected to the processor, wherein the processor executable code further configures the processor to:

compare the location of the confocal plane to a calibrated confocal plane location associated with a location of the corresponding one of the one or more slit aperture filters stored in the data storage element; and adjust the location of the confocal plane to the calibrated confocal plane location.

13. The apparatus of claim 7, wherein the processor executable code further configures the processor to:

receive one or more illumination line image signals from the one or more position detectors;

analyze the one or more illumination line image signals to determine a position of the illumination line image; and adjust a position of a corresponding slit aperture filter such that a slit of the slit aperture filter is centered on the illumination line image in an x-direction.

14. The apparatus of claim 7, wherein the processor executable code further configures the processor to:

receive one or more illumination line image signals from the one or more position detectors;

analyze the one or more illumination line image signals to determine a position of the illumination line image; and adjust a position of a corresponding slit aperture filter such that a slit of the slit aperture filter is centered on the illumination line image in an x-direction.

* * * * *